US007908231B2

(12) United States Patent
Miller

(10) Patent No.: US 7,908,231 B2
(45) Date of Patent: Mar. 15, 2011

(54) SELECTING A CONCLUSION USING AN ORDERED SEQUENCE OF DISCRIMINATORS

(76) Inventor: James R. Miller, Surprise, AZ (US)

(*) Notice: Subject to any disclaimer, the term of this patent is extended or adjusted under 35 U.S.C. 154(b) by 841 days.

(21) Appl. No.: 11/761,878

(22) Filed: Jun. 12, 2007

(65) Prior Publication Data

US 2008/0313223 A1 Dec. 18, 2008

(51) Int. Cl.
*G06E 1/00* (2006.01)
*G06E 3/00* (2006.01)
*G06G 7/00* (2006.01)
*G06F 15/18* (2006.01)

(52) U.S. Cl. ............................................... 706/16
(58) Field of Classification Search .................. 706/16
See application file for complete search history.

(56) References Cited

U.S. PATENT DOCUMENTS

| 6,004,267 | A | 12/1999 | Tewari et al. |
| 6,247,004 | B1 | 6/2001 | Moukheibir |
| 6,375,614 | B1 | 4/2002 | Braun et al. |
| 6,520,910 | B1 | 2/2003 | Kohls |
| 6,754,655 | B1 | 6/2004 | Segal |
| 2003/0207278 | A1 | 11/2003 | Khan et al. |
| 2003/0219715 | A1 | 11/2003 | Lam et al. |
| 2005/0149268 | A1 | 7/2005 | Sharp |
| 2005/0209785 | A1 | 9/2005 | Wells et al. |
| 2005/0262031 | A1 | 11/2005 | Saidi et al. |
| 2005/0280809 | A1* | 12/2005 | Hidai et al. ............... 356/237.3 |
| 2005/0282199 | A1 | 12/2005 | Slawin et al. |
| 2006/0135855 | A1 | 6/2006 | Alsafadi et al. |
| 2006/0195269 | A1 | 8/2006 | Yeatman et al. |
| 2006/0289020 | A1 | 12/2006 | Tabak et al. |
| 2007/0009970 | A1 | 1/2007 | Heller et al. |
| 2007/0233435 | A1* | 10/2007 | Bradski ............................ 703/2 |

FOREIGN PATENT DOCUMENTS

JP 05-277119 10/1993
JP 2004-185547 7/2004

OTHER PUBLICATIONS

Yohannes et al. "Classification and Regression Trees: An Introduction", Technical Guide #3, IFPRI, 1999, pp. 1-29.*

* cited by examiner

*Primary Examiner* — Michael B. Holmes
*Assistant Examiner* — Li-Wu Chang
(74) *Attorney, Agent, or Firm* — Alex Starkovich

(57) ABSTRACT

A method for data analysis according to various aspects of the present invention generally includes selecting a conclusion from a plurality of conclusions for one or more test data sets by generating discriminators from one or more threshold indicators associated with the conclusion, selecting a portion of the discriminators, ranking the discriminators in a sequence, and applying the sequence of discriminators to one or more test data sets to select the conclusion.

24 Claims, 4 Drawing Sheets

SELECTING A CONCLUSION USING AN ORDERED SEQUENCE OF DISCRIMINATORS

DESCRIPTION OF THE INVENTION

1. Field of the Invention

The present invention relates to systems and methods for data analysis.

2. Background of the Invention

In a variety of fields and situations, it is useful to draw a conclusion based on a set of empirical data. There are many situations in science, engineering, medicine, and other fields where it is desirable to conclude which of a set of possible conditions or states exist, or predict which of a set of possible events will occur in the future. For example, it may be advantageous to be able to analyze a set of data from one or more patients in order to diagnose whether any of them has a particular disease, or to analyze data to determine which patients are likely to develop a disease in the future.

Conventional data analysis methods used to make an inference based on a set of data may include a number of drawbacks. For example, conventional data analysis methods may not be able to properly identify which indicators associated with a set of data are most determinative in making a particular diagnosis, resulting in misdiagnosing an event or condition. Additionally, conventional data analysis methods may not be able to properly utilize indicators relevant to a conclusion in selecting the conclusion. These and other issues are addressed by the embodiments of the present invention.

BRIEF SUMMARY OF THE INVENTION

A method for data analysis according to various aspects of the present invention generally includes selecting one or more conclusions appropriate to one or more training data sets by generating discriminators from one or more threshold indicators associated with those conclusions, selecting a portion of the discriminators, ranking and sequencing the discriminators, and applying the ranked sequence of discriminators to one or more test data sets to select one or more conclusions appropriate to the test data.

It is to be understood that both the foregoing general description and the following detailed description are exemplary and explanatory only and are not restrictive of the invention, as claimed.

BRIEF DESCRIPTION OF THE DRAWINGS

A more complete understanding of the present invention may be derived by referring to the detailed description and claims when considered in connection with the following illustrative figures.

DETAILED DESCRIPTION OF EXEMPLARY EMBODIMENTS

Figure 1:
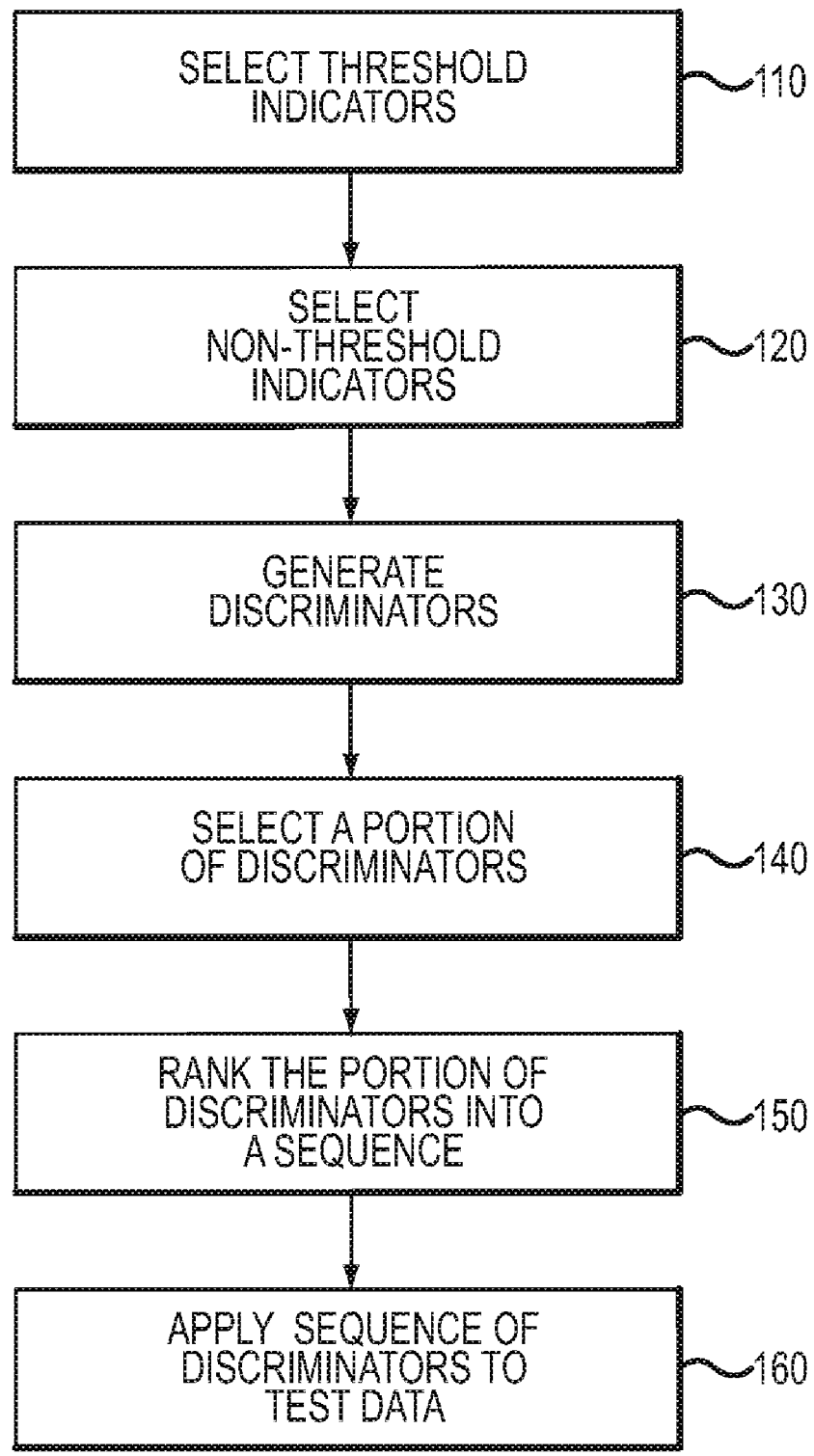
FIG. 1 is a flow diagram depicting an exemplary process for data analysis according to various aspects of the present invention.

Systems and methods according to aspects of the present invention may be applied to any situation and context to select a conclusion from a set of possible conclusions based on empirical data. For example, the present invention may be used to conclude which of a set of possible conditions or states of the world pertains, which of two interpretive definitions of a situation is more appropriate, which of a set of possible events will occur in the future, whether or not a particular future event will occur, or in any other situation or context to select a conclusion from a set of possible conclusions.

In systems and methods according to various aspects of the present invention, a conclusion is selected based on one or more indicators based on empirical evidence. An indicator may relate to any form of measurable evidence in any manner. An indicator may be derived directly from an observable phenomenon, or may be inferred indirectly from such an observation. For example, a conclusion that a patient has a particular disease may be inferred based one or more indicator symptoms directly observed in the patient. Alternatively, a conclusion that a subject who has just suffered a first heart attack will suffer another one within the next five years may be forecast indirectly on the basis of various indicators such as the subject's family history, medical record, diet, and the like.

Where one conclusion is of particular interest, it may be referred to as the focal conclusion. The focal conclusion can have any number of alternate conclusions, i.e. any conclusion other than the focal conclusion. For example, the focal conclusion may be that a patient has cancer, and one possible alternate conclusion is that the patient does not have cancer. An alternate conclusion need not necessarily constitute the sole contradiction of the focal conclusion, an alternate conclusion is simply other than and inconsistent with the focal conclusion. For example, for the focal conclusion that a patient has lung cancer, alternate conclusions could be that the patient has only thyroid cancer, that the patient has only skin cancer, that the patient has only pancreatic cancer, and that the patient has no cancer whatsoever.

In accordance with various aspects of the present invention, indicators and the conclusions to which they relate may apply to any desired situation, event, field of study, state, condition, and/or the like. For example, In addition to the diagnosis and prediction of disease or other medical conditions, the present invention may be used in conjunction with a variety of financial situations, such as a conclusion as to whether or not a loan will be repaid based on indicators derived from the debtor's loan application.

An indicator can include anything related to the measurement and/or observation of any type of empirical phenomenon. An indicator may be of any form, such as: a numeric or non-numeric value; a mathematical function; any type of statement regarding a condition, event, result, state of being, etc.; and/or the like.

An indicator includes some form of measurement scale. Indicators may be valued using any suitable measurement scale, such as a rating or scoring system, a form of categorization, and/or the like. For example, an indicator may include measurement values on a numeric scale, such as the size of a skin lesion as an indicator of skin cancer. An indicator may also include measurement values on a non-numeric scale, such as an indicator of academic success for a student classified as "pass" or "fail" or a conditional statement classified as "true" or "false." Indicators may also be valued using any combination of numeric and non-numeric measurement scales.

Some indicators, known as threshold indicators, have a dichotomous threshold-like relationship to the conclusion being sought. In a simple example, indicators related to whether or not a person should legally be allowed to purchase alcohol may include the age of consumption in a statute. That is, if the purchaser is 21 or older, they should be allowed to purchase alcohol, while if they are under 21 they should not. Another example of a threshold indicator could be the "pass" or "fail" classification for concluding the academic success of a student. In yet another example, where the rank of a military officer may be Lieutenant, Captain, Major, Colonel, or General, the officer's rank may be an indicator for inferring a conclusion as to whether the officer's length of military service is greater than three years. As with the measurement scale of an indicator, thresholds may include numeric and non-numeric values.

The specific value of threshold indicators above or below the threshold does not have a bearing on the conclusion being sought. For example, the specific age of a person is irrelevant to the conclusion as to whether that person should be allowed to purchase alcohol, only whether their age is equal or greater than the threshold age of 21. Similarly, a student's exact level of academic success for an indicator using a "pass" or "fail" classification is irrelevant. The measurement scale for a threshold indicator consistently supports a conclusion on one side of the threshold. For example, a person at any age under 21 should not legally be allowed to purchase alcohol, where a person age 21 or over should. In other words, the association between points in a measurement scale on one side of a threshold value and a conclusion is unidirectional. All points in a scale on the same side of a threshold value point in the same direction (i.e., toward the same conclusion). A threshold value can be selected for an indicator at any suitable point in its measurement scale).

Other indicators, known as non-threshold indicators, have a different relationship to the conclusion being sought. Non-threshold indicators may include multiple categories or levels of the indicator that relate to the conclusion, and may possess a quantitative relationship to the conclusion throughout an entire range of the indicator's scale values. For example, an indicator for the likelihood of repayment of a loan may depend on which of three levels of disposable income the applicant can anticipate during the repayment period: "inadequate" (suggesting a low likelihood of repayment); "marginally adequate" (suggesting an intermediate likelihood of repayment); or "fully adequate" (suggesting a high likelihood of repayment).

A non-threshold indicator may include any suitable number of separate categories, component scale values, and/or the like, which may be selected in any desired manner. As with threshold indicators, non-threshold indicators may be valued numerically, non-numerically, or a combination of the two. For example, a great deal of research has shown that the thickness (in millimeters) of a patient's primary skin lesion is a key indicator with both diagnostic and prognostic significance for melanoma. Tumor thickness is typically divided into four categories, each including a numerical range of thicknesses, as follows:

Category 1: very thin (no more than 1 millimeter);
Category 2: moderately thin (more than 1, but no more than 2 millimeters);
Category 3: moderately thick (more than 2, but no more than 4 millimeters); and
Category 4: very thick (more that 4 millimeters).

In some cases, threshold indicators may be generated from non-threshold indicators. For example, where sub-portions of the measurement scale for a non-threshold indicator are consistently related to a conclusion (but the measurement scale overall does not), the non-threshold indicator may be separated into multiple threshold indicators that include the appropriate sub-portions. Another, more common way to generate threshold indicators from non-threshold indicators is to partition a non-threshold indicator's scale of values into just two distinct ranges. Research has shown that very thick tumors (category 4, above) are decidedly more indicative of poor future outcomes for melanoma patients than any of the thinner categories. Hence, possessing a very thick primary tumor is sometimes characterized as a high-risk prognostic factor, while possessing any thinner tumor category is characterized as lower-risk.

FIG. 1 depicts an exemplary method for data analysis according to various aspects of the present invention. In this exemplary method, threshold indicators are selected (110), along with non-threshold indicators (120). Discriminators are generated both from the originally selected threshold indicators and from the non-threshold indicators that have been converted into threshold indicators (130). A portion of the discriminators are selected (140) and ranked into a sequence (150). The sequence is applied to one or more sets of test data to select conclusions (160).

Select Threshold Indicators 110

A set of threshold indicators may be selected (110) from any suitable source according to any desired criteria, such as the relation of a given indicator to a conclusion being sought and/or the propensity of the indicator to indicate a conclusion. For example, where a conclusion as to whether a patient has a particular disease is sought, threshold indicators may be selected according to a review of medical journals and research to identify those indicators most relevant to the diagnosis of that disease. A set of threshold indicators may also be generated and/or provided (in whole or in part) from any source and in any manner for use in the present invention.

Figure 2A:
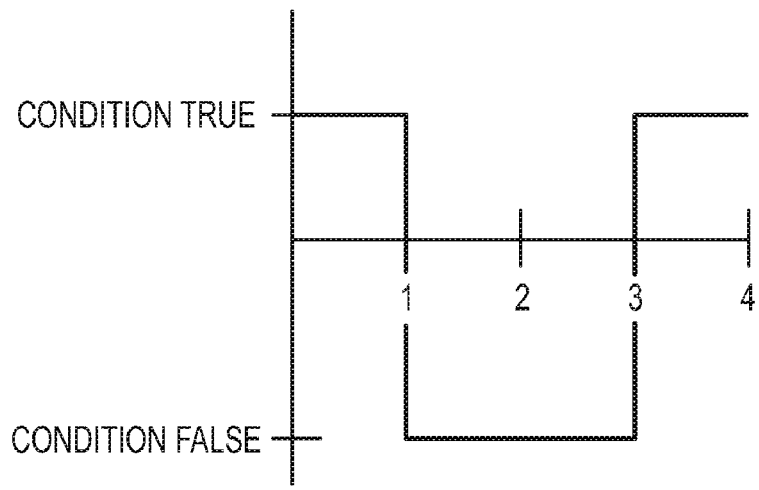
FIG. 2A is a plot of an exemplary non-threshold indicator.

Threshold indicators have a relationship to the conclusion being sought and a measurement scale in terms of which a threshold value can be defined, wherein the points in the measurement scale on the two sides of the threshold value are consistent with two separate conclusions. Any number of threshold indicators having any form may be selected and used in conjunction with the present invention. For example, as discussed previously, threshold indicators may be generated from non-threshold indicators. A plot for an arbitrary, exemplary non-threshold indicator is depicted in FIG. 2A. In this example, the indicator has multiple relationships to a condition (true or false) over its measurement scale (0 to 4), depending on the particular value of the indicator as follows:

$0 < \text{Value} \leq 1$: The indicator relates to a true condition;
$1 < \text{Value} \leq 3$: The indicator relates to a false condition; and
$3 < \text{Value} \leq 4$: The indicator relates to a true condition.

Figure 2B:
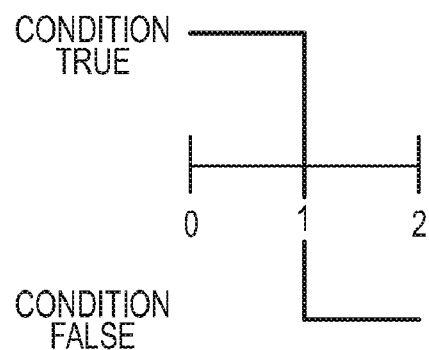
FIGS. 2B and 2C are plots of exemplary threshold indicators based on the non-threshold indicator in FIG. 2A.
Figure 2C:
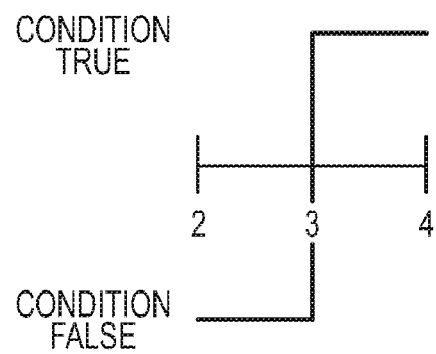

As can be seen, no single threshold value can be selected for the indicator for which there would be a consistent relationship to either the true or false condition throughout the entire measurement scale on either side of the threshold. However, the indicator depicted in 2A can be separated into two separate threshold indicators as shown in FIGS. 2B and 2C. In FIG. 2B, a threshold indicator having a measurement scale of 0 to 2 and a threshold at 1 is shown, where:

$0 < \text{Value} \leq 1$: The indicator relates to a true condition; and
$1 < \text{Value} \leq 2$: The indicator relates to a false condition.

In FIG. 2C, a threshold indicator having a measurement scale between 2 and 4 and a threshold at 3 is shown, where:

$2 < \text{Value} \leq 3$: The indicator relates to a false condition; and
$3 < \text{Value} \leq 4$: The indicator relates to a true condition.

Threshold indicators generated from non-threshold indicators may in turn be used to generate discriminators as discussed below. Threshold indicators may also include results from one or more alternate data analysis procedures performed on a set of data (such as a training data set as discussed below). For example, a threshold indicator may include the result from an analysis performed on a training data set by a neural net or other diagnostic procedure.

A threshold indicator includes a threshold value (also commonly known as a cut-point) along the measurement scale of the indicator to discriminate between a conclusion on one side of the threshold and a conclusion on the other side of the threshold. The threshold value may be selected according to any desired criteria, such as to maximize a desired performance standard for a diagnostic test. For example, the threshold may be selected to maximize a desired level of sensitivity and specificity for a particular test. In a diagnostic test, members of a data set that are correctly diagnosed positive are known as true positives, while those that are actually positive but are diagnosed negative are known as false negatives. Similarly, members of a data set that are correctly diagnosed negative are known as true negatives, while those that are actually negative and diagnosed positive are known as false positives. The sensitivity of a test generally refers to the proportion of data set members that test positive out of all the members that are actually positive (which includes both true positives and false negatives), while specificity generally refers to the proportion of data set members that test negative out of all the members that are actually negative (which includes both true negatives and false positives).

For example, in a diagnostic test for pregnancy, a positive test result indicates that the woman taking the test is pregnant while a negative test indicates the woman is not pregnant. The two diagnostic conclusions are thus pregnancy versus non-pregnancy. In this example, the diagnostic test results may be based on the concentration of a hormone in a woman's blood known to be associated with pregnancy. Relatively high concentrations of the hormone indicate pregnancy, while relatively low or zero concentrations of the hormone indicate a woman is not pregnant. A threshold/cut-point value may be selected in the scale of the hormone concentration threshold indicator that will define a positive (high concentration) versus a negative (low or zero concentration) test result. Relative to any given cut-point, the sensitivity of the pregnancy test is then defined as the proportion of actually pregnant test-takers who obtain a correct positive (at or above the cut-point) test result. Relative to the same cut-point, the specificity of the pregnancy test is the proportion of actually non-pregnant test-takers who obtain a correct negative (below the cut-point) test result.

In accordance with the present invention, a maximum weighted average of the sensitivity and specificity proportions (as opposed to a simple, unweighted mean) may be used as a criterion in selecting the optimum threshold cut-point value. For example, in the pregnancy test example above, an optimum cut-point may be selected to favor sensitivity and thereby reduce the number of pregnancies that go undetected. An optimum cut-point may be selected according to any other desired balance between sensitivity and specificity, such as to maximize specificity while achieving a minimum level of sensitivity, or vice versa.

Threshold indicators and their thresholds/cut-points may be selected in accordance with the present invention in any manner and according to any other desired criteria, such as by using one or more statistical techniques. For example, logistic regression may be used to determine whether, and to what extent, the measured values of a threshold indictor (or non-threshold indicator that has been converted into one or more threshold indictors) are applicable to one or more conclusions. Any other suitable method may be used to determine whether an indicator is statistically associated with one or more conclusions.

In addition to selecting threshold indicators (110), the exemplary process depicted in FIG. 1 may also select non-threshold indicators (120). Any number of non-threshold indicators of any form may be selected. Non-threshold indicators may be selected in any manner according to any criteria, and may also be generated and/or provided in any manner. For example, a non-threshold indicator may be selected based on a probability that the non-threshold indicator is indicative of one or more conclusions. A set of non-threshold indicators may also be provided (in whole or in part) from any source for use in the present invention. For example, non-threshold indicators may include results from one or more alternate data analysis procedures performed on a set of data (such as a training data set as discussed below), such as an analysis performed by a neural net or other diagnostic procedure.

Non-threshold indicators can be selected in accordance with the present invention through commonly-known statistical analysis procedures, such as logistic regression. Logistic regression analysis may be appropriate when there are only two possible conclusions to select from. Any number and/or type of analyses may be performed to select non-threshold indicators. For example, non-threshold indicators may be analyzed using a series of univariate and multivariate logistic regression analyses in order to select only those indicators that are consistent with previous research and/or a known relationship between an indicator and a conclusion. In one possible example, univariate logistic regression analyses may be performed on a set of non-threshold indicators to determine how each is related to the focal conclusion and its single alternate conclusion. Logistic regression analyses may utilize a set of historical data from one or more data sources for each non-threshold indicator, where the conclusion sought (focal or alternative) is known for each data source. Such a data set may be referred to as a training data set. The input (independent variables) to the logistic regression is the set of non-threshold indicators, while the dependent variable is whether the focal or alternate conclusion applies. The output of the logistic regression analysis is the probability that each indicator is indicative of the focal versus the alternate conclusion. Logistic regression may also provide a measure of the statistical significance between the correct conclusion (the dependent variable) and the non-threshold indicators (the independent variables), as well as the statistical significance of each non-threshold indicator. The probabilities generated by logistic regression analysis for non-threshold indicators may, themselves, be used in accordance with the present invention to select one or more conclusions for a test data set. For example, traditional prognostic risk factors indicative of distant metastasis in melanoma, such as tumor thickness, ulceration, and mitotic rate, could be the inputs (independent variables) of a multivariate logistic regression. Its dependent variable could be the detection or non-detection of distant metastasis within some specified span of years. From this analysis a probability of distant metastasis may be derived for each patient. These probabilities could then be converted to a threshold indicator by locating the cut-point among them with maximum prognostic discriminating ability and incorporated into the present invention. Additionally, as discussed previously, non-threshold indicators may be used in other ways, such as to generate multiple threshold indicators.

As shown in the exemplary process according to aspects of the present invention depicted in FIG. 1, a set of threshold and/or converted non-threshold indicators can be used to generate a set of discriminators (130). Discriminators are conditional statements—a pair of such statements relating to each threshold indicator. Discriminators may be expressed in any manner, such as through a mathematical equation, sentence or phrase, or in any suitable manner. Discriminators according to various aspects of the present invention may be of any suitable form, and may relate to an indicator in any appropriate manner. Discriminators can relate to any measurement scale of an indicator, either numeric or non-numeric.

In the case of threshold indicators, discriminators are associated with the ranges on either side of a cut-point in its measurement scale, where the ranges relate to one or more conclusions, such as a focal conclusion and an alternative conclusion. The discriminators for each threshold indicator may comprise a pair of mutually-exclusive and collectively exhaustive conditional statements. For example, a threshold indicator of a person's age may relate to the conclusion that they should legally be allowed to purchase alcohol. In this example, the focal conclusion could be that the person should legally be allowed to purchase alcohol, while the alternate conclusion could be that the person should not. In this example, the indicator may be used to generate the following two discriminators:

If the Person's Age$\geqq$21, Person is allowed to buy alcohol
If the Person's Age<21, Person is not allowed to buy alcohol The pair of discriminators for a threshold indicator, such as the ones in this example, may be generated to be mutually exclusive and collectively exhaustive to allow a definite conclusion to be drawn from measured test data within the measurement range of the indicator. Where two mutually exclusive and collectively exhaustive discriminators are generated from a threshold indicator, one discriminator can be associated with the range of values on one side of the threshold value indicative of the focal conclusion, with the other discriminator being associated with the range of values on the other side of the threshold value indicative of one or more alternate conclusions.

In the case of non-threshold indicators, multiple pairs of mutually exclusive and collectively discriminators can be generated from a single non-threshold indicator in accordance with the present invention. Referring again to FIGS. 2A, 2B, and 2C, a single non-threshold indicator (shown in FIG. 2A) is used to generate two separate threshold indicators, shown in FIGS. 2B and 2C. A pair of discriminators for the threshold indicator depicted in FIG. 2B are:

If 0<Value$\leqq$1, the condition is true;
If 1<Value$\leqq$2, the condition is false.

While a pair of discriminators for the indicator in FIG. 2C are:

If 2<Value$\leqq$3, the condition is false;
If 3<Value$\leqq$4, the condition is true.

In the examples depicted in FIGS. 2B and 2C, it can be seen that the discriminators are mutually exclusive and collectively exhaustive over the measurement range of their respective threshold indicators.

In the exemplary process depicted in FIG. 1, a portion of the discriminators is selected (140) and ranked into a sequence (150). Any portion of the discriminators generated from a set of indicators (including all the discriminators) may be selected and ranked according to any desired criteria. Discriminators may be selected and ranked based on their propensity to indicate one or more conclusions for a training data set. For example, in one exemplary embodiment of the present invention employed to select either a focal conclusion or one or more alternate conclusions, the selection (140) and ranking (150) of a portion of discriminators may be based at least partially on each discriminator's propensity to distinguish between the focal conclusion and the one or more alternate conclusions based on data in a training data set.

A training data set can be any set of measurements statistically associated with one or more conclusions. In accordance with the present invention, a training data set may include measurements for one or more threshold or non-threshold indicators. The training data set shows the relation between measurements for one or more indicators and one or more conclusions. The data in the training data set can come from any number or type of appropriate data sources. For example, data sources could include one or more patients, each of which provides one or more elements of data relating to a disease to the training data set. Data sources could also include individual loans containing data relating to whether a loan is likely to be paid. Each individual data source for a training data set may contribute any number and type of data measurements. For example, data for a patient may include the patient's age, weight, blood pressure, medical history, and other health statistics. A training data set may also include data from previous test data sets used in conjunction with the present invention.

The conclusion(s) sought in accordance with the present invention are preferably known for each data source in the training data set. For example, where the conclusion at issue is that a disease is present, a training data set that includes health statistics for one or more patients also includes whether or not each patient actually has the disease. Discriminators may thus be applied to the data in the training data set to determine the propensity for each discriminator to correctly indicate one or more (known) conclusions. Similarly, the indicators from which the discriminators are generated may be analyzed with reference to the training data set to determine whether the range of measurement values for the indicators themselves are statistically associated with one or more conclusions. Data sources for which the conclusion(s) sought are not known may be excluded from consideration.

Figure 3:
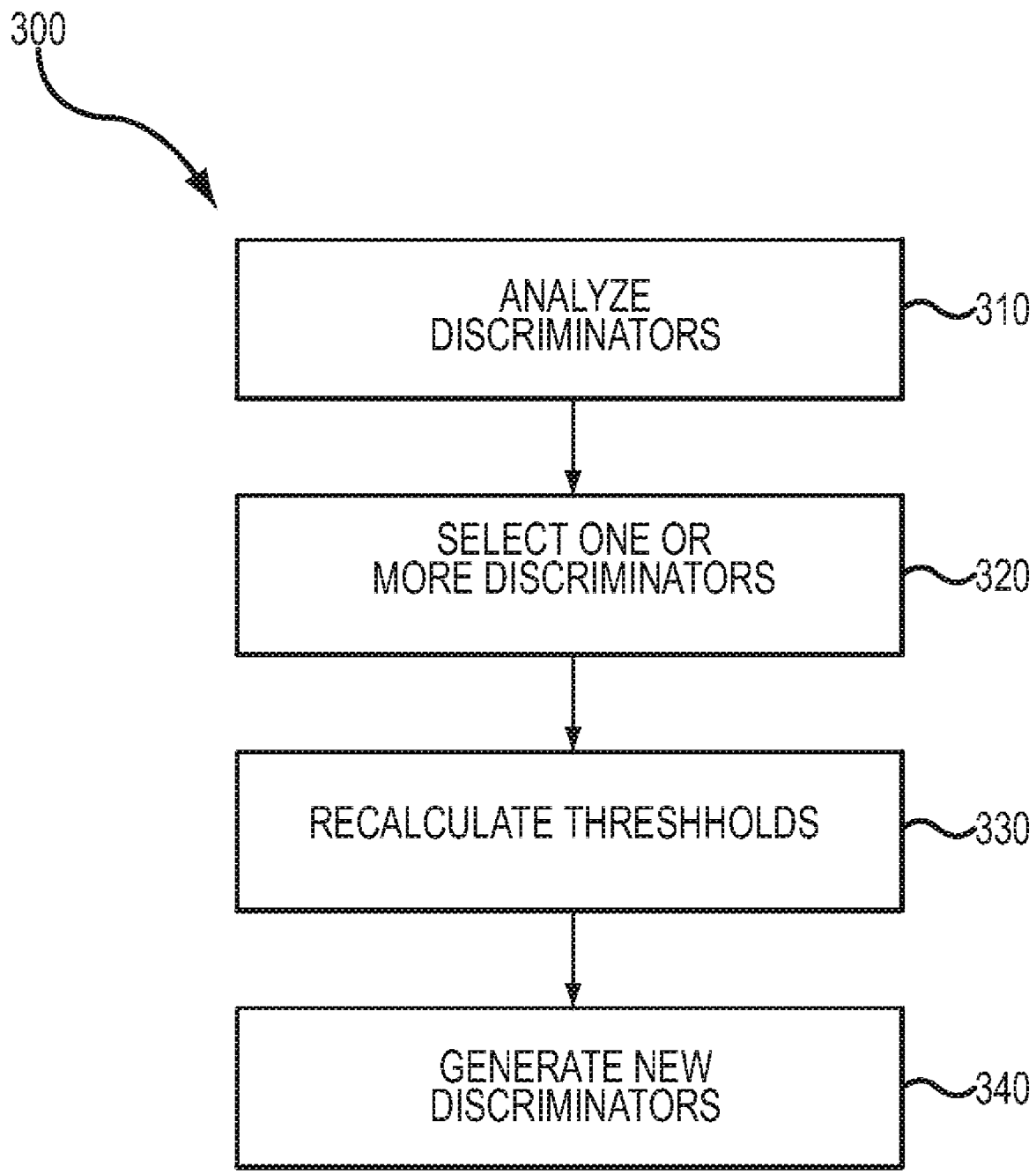
FIG. 3 is a flow diagram of an exemplary process for selecting and ranking discriminators according to various aspects of the present invention.

A portion of discriminators may be selected and ranked in any order and in any manner. For example, discriminators may be selected and ranked separately, or selected and ranked as part of the same process. FIG. 3 depicts an exemplary process (300) for selecting (140) and ranking (150) discriminators according to various aspects of the present invention. In this exemplary process, discriminators can be selected and ranked iteratively based on each discriminator's propensity to indicate a conclusion. In this exemplary embodiment, discriminators are analyzed (310) to determine which discriminator(s) should be selected on the current iteration of the process (300), and one or more discriminators are selected (320). The analysis of the discriminators (310) may be performed in any manner according to any criteria. For example, an analysis of the discriminators (310) may identify the discriminator that has the highest propensity for indicating a correct conclusion for the data sources for a training data set. Additionally, such an analysis may identify the discriminator that achieves the maximum net improvement in the range of weighted average sensitivity and specificity proportions with respect to the data sources.

For example, in a case where a discriminator is analyzed to determine its relation to the sensitivity and specificity for data sources indicative of either a focal or alternate conclusion, a discriminator that indicates the focal conclusion increases the minimum achievable overall weighted sensitivity proportion when it indicates the focal conclusion correctly for a data source (a true positive). On the other hand, the discriminator decreases the maximum achievable overall weighted specificity proportion when it indicates the focal conclusion incorrectly for a data source (a false positive). Similarly, a discriminator that indicates the alternate conclusion increases the minimum achievable overall weighted specificity proportion when it indicates the alternative conclusion correctly (a true negative), and decreases the maximum achievable overall weighted sensitivity proportion when it indicates the alternate conclusion incorrectly (a false negative). Discriminators that reduce the net improvement in some combination of specificity and sensitivity may be excluded from selection. Alternatively, the discriminators with the least reduction in sensitivity or specificity may be selected, such as in a case where no discriminator provides a net improvement to some combination of sensitivity and specificity for a data source. Discriminators may be selected and ranked based on their ability to meet a certain threshold of sensitivity and/or specificity while also exhibiting the highest propensity to indicate a correct conclusion for a data source of the training data set.

In the exemplary discriminator selection and ranking process (300) depicted in FIG. 3, discriminators are selected and ranked in the order in which they achieve the most accurate indications of a conclusion for a training data set. The selection of a discriminator (320) removes that discriminator from the pool of generated discriminators, as well as from consideration in further iterations of the discriminator selection and ranking process (300). Additionally, the data sources for which the discriminator indicates a conclusion may be removed from further consideration with regards to the unselected discriminators in future iterations of the selection and ranking process (300). For example, if a training data set has 1000 data sources, and the first selected discriminator indicates a conclusion for 400 of them, future iterations of the selection and ranking process (300) for the other discriminators may be applied to only the remaining 600 data sources. By removing data sources for which a conclusion is indicated by a discriminator at each iteration of the selection and ranking process (300), the selection of irrelevant and/or conflicting discriminators can be avoided.

Any number of discriminators may be selected and ranked in a single iteration of the exemplary process (300) depicted in FIG. 3. The thresholds of the indicators that did not generate any of the selected discriminators (on any previous iteration) may be recalculated (330) and new discriminators generated from the modified thresholds (340). Recalculation of the cut-points (thresholds) for indicators may be performed in any manner based on any criteria. For example, the prognostic significance of a patient's estrogen level in terms of contracting breast cancer may differ considerably by the sex of the patient. Most breast cancer patients are female, but some are male. Once a discriminator related to the sex of the patient has been selected, the composition of as yet unselected patients will shift to include exclusively the other sex. Now, the appropriate cut-point for estrogen level defining its pair of discriminators can then be re-calculated strictly on the basis of the as yet unselected patients of the other sex.

The iterative process for discriminator selection depicted in FIG. 3 may repeat until all discriminators are selected, all data sources have been removed from consideration, a determination is made that the selection of additional discriminators will not improve the sensitivity and/or specificity for a data source, and/or until any other suitable condition or criterion is satisfied. For example, successive discriminators providing ever-lower net improvements in weighted average sensitivity and specificity may be selected until the net improvement becomes negative. Selecting any additional discriminators would reduce the weighted average by drawing too many additional conclusions that are false. However, stopping, here, might leave as yet unselected patients without any diagnosis. An alternative stopping rule would be to proceed until all patients have been diagnosed, but in a sequence that minimizes the incremental damage done to weighted average sensitivity and specificity by adding these extra patients.

The sequence of discriminators is applied to one or more test data sets (160) to select conclusions regarding the one or more test data sets. The test data set contains corresponding data for the selected indicators. Aside from this, a test data set may include any type of data from any source, and may be generated and/or provided (in whole or in part) in any manner. A test data set need not contain the same number, type, or compositionally representative data sources as a training data set used to select and rank the sequence of discriminators.

Application of the sequence of discriminators to a test data set results in one or more conclusions being selected for the test data set. There may also be one or more data sources for which no conclusion could be drawn, due to factors such as insufficient or incorrectly measured data. Probabilities of the accuracy of the indication of one or more conclusions for each data source contained in the test data set may be generated in order to assess the ability of the sequence of discriminators to select the one or more conclusions (e.g., to make diagnoses, prognoses, predictions, characterizations, etc.). The probabilities of the accuracy of the indicated conclusions can give a reference as to how effectively the discriminator sequence, optimized on the basis of the training data, operates on separate data drawn from one or more (possibly unrelated) test sets.

Any other metric, statistic, and/or the like may be calculated for the results of the application of the sequence of discriminators on one or more test data sets. For example, a weighted average of the sensitivity and specificity proportions can be calculated for the test data set to compare to the weighted averages calculated for a training data set. Additionally, the number of data sources, if any, for which no conclusion can be drawn is also noted for each test set.

Methods for data analysis according to various aspects of the present invention may be implemented in any manner, such as through a software program operating on a computer system. Such a software program may be stored on any computer-readable medium, such as floppy disks, hard disks, CD-ROMs, DVDs, any type of optical or magneti-optical disks, volatile or non-volatile memory, and/or any other type of media suitable for storing electronic instructions and capable of interfacing with a computing device. The method according to aspects of the present invention may operate in conjunction with any type of computer system, such as a personal computer (PC), server, cellular phone, personal digital assistant (PDA), portable computer (such as a laptop), embedded computing system, and/or any other type of computing device. The computer system may include any number of computing devices connected in any manner, such as through a distributed network. The computer system may communicate and/or interface with any number of users and/or other computing devices to send and receive any suitable information in any manner, such as via a local area network (LAN), cellular communication, radio, satellite transmission, a modem, the Internet, and/or the like.

Figure 4:
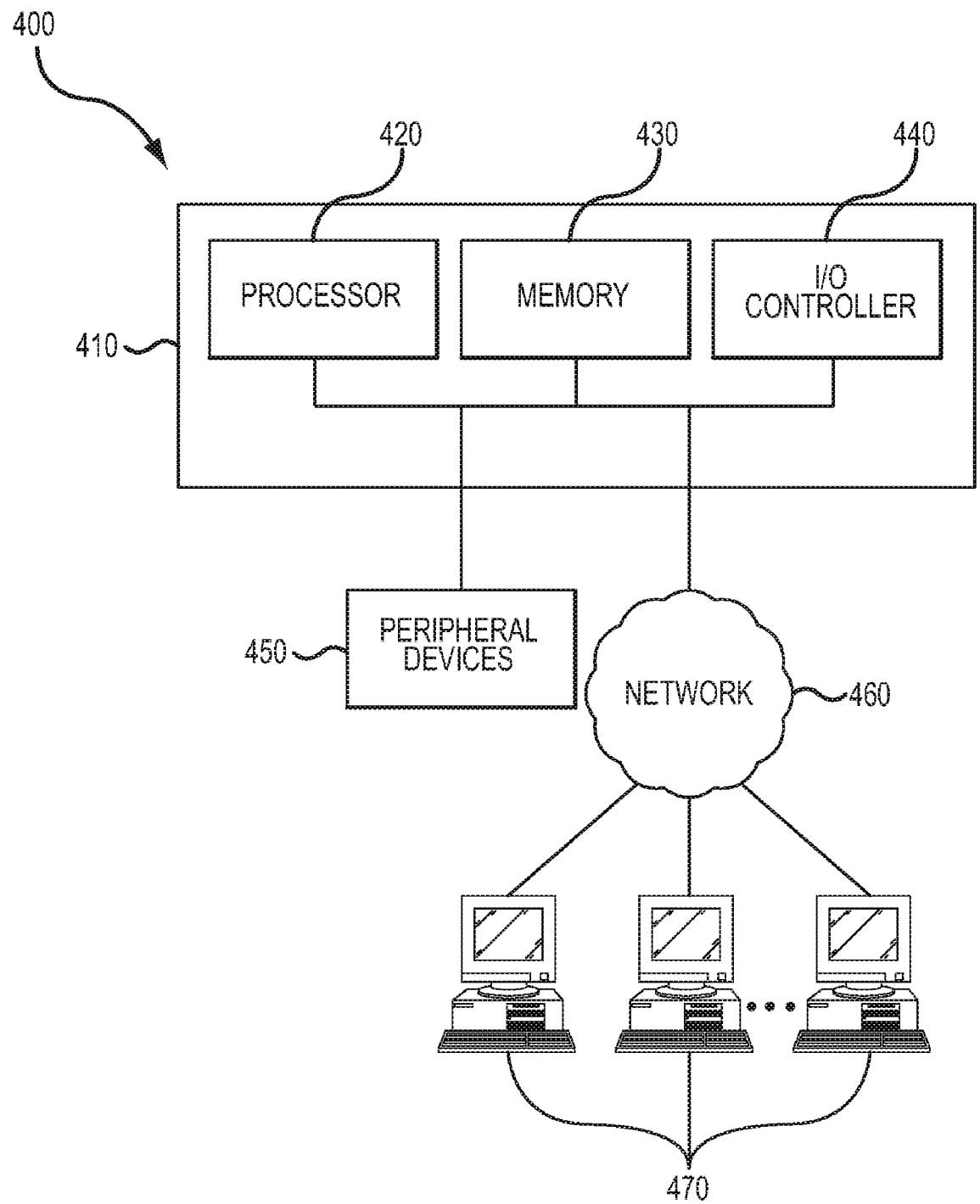
FIG. 4 is a block diagram of an exemplary system for data analysis according to various aspects of the present invention.

For example, FIG. 4 depicts an embodiment of a system for data analysis 400 according to various aspects of the product invention. In this exemplary embodiment, the system 400 includes a computer system 410, which includes a processor 420, memory 430, and input/output (I/O) controller 440. The computer system 410 may communicate with one or more peripheral devices 450 as well as with one or more additional computing devices 470 through a network 460.

The computer system 410 may store a software program configured to perform a method for data analysis in the memory 430 and run the software program using the processor 420. The computer system 410 may include any number of individual processors 420 and memories 430. Indicators, training and test data sets, and other information may be provided to the computer system 410 by a user through the one or more peripheral devices 450 controlled by the I/O controller 440. Such information may also be provided from other computing devices 470 connected to the computer system 410 through a network 460. The computer system 410 may allow provided indicators to be processed by the software program and displayed to various peripheral devices 450 (such as monitors and printers). The software program may be controlled and interacted with in any manner by a user through other peripheral devices 450 (such as a mouse and keyboard).

The computer system 410 may include any number of processors 420, memory devices 430, I/O controllers 440 and any other suitable components, devices, and/or systems. The computer system 410 may interface with any number or type of suitable peripheral devices 450, such as a mouse, keyboard, monitor, speakers, printer, external memory device, and/or any other system or device. The computer system may communicate with other systems and devices over any type of network 460, such as a local area network (LAN), wide area network (WAN), the Internet, and the like. A system for data analysis 400 may operate in conjunction with any other systems and devices, such as one or more computing devices 470, or any other system or device.

The particular implementations shown and described above are illustrative of the invention and its best mode and are not intended to otherwise limit the scope of the present invention in any way. Indeed, for the sake of brevity, conventional data storage, data transmission, and other functional aspects of the systems may not be described in detail. Furthermore, the connecting lines shown in the various figures are intended to represent exemplary functional relationships and/or physical couplings between the various elements. Many alternative or additional functional relationships or physical connections may be present in a practical system.

Changes and modifications may be made to the disclosed embodiment without departing from the scope of the present invention. These and other changes or modifications are intended to be included within the scope of the present invention, as expressed in the following claims.

What is claimed is:

1. A method for selecting a conclusion from a plurality of conclusions, the method comprising:
generating, by a computer system, a plurality of discriminators from one or more provided threshold indicators associated with the conclusion, wherein the plurality of discriminators includes a pair of mutually exclusive and collectively exhaustive discriminators for each of the one or more provided threshold indicators;
selecting a portion of the plurality of discriminators; and
ranking the portion of the plurality of discriminators to create an ordered sequence of discriminators, wherein the ordered sequence of discriminators is for selecting the conclusion for one or more test data sets;
wherein at least one of selecting and ranking the portion of the plurality of discriminators includes:
recalculating thresholds for one or more indicators; and
generating new discriminators based on the recalculated thresholds.

2. The method of claim 1, wherein both the selecting and ranking of the portion of the plurality of discriminators is based at least partially on each discriminator's propensity to indicate one or more of the plurality of conclusions for at least one training data set.

3. The method of claim 1, wherein generating the plurality of discriminators includes selecting a threshold for each of the one or more provided threshold indicators.

4. The method of claim 2, wherein at least one of the threshold indicators comprises a result of a data analysis procedure performed on the training data set.

5. The method of claim 2, wherein the training data set comprises a plurality of data sources.

6. The method of claim 1, further comprising selecting the one or more provided threshold Indicators.

7. The method of claim 6, wherein selecting the one or more provided threshold indicators is at least partially based on at least one of a desired sensitivity, a desired specificity, and on each provided indicator's propensity to indicate one or more of the conclusions from the plurality of conclusions.

8. The method of claim 6, wherein selecting the one or more provided threshold indicators includes determining whether a threshold indicator includes a plurality of measurement values, the measurement values being mutually exclusive and collectively exhaustive.

9. The method of claim 8, wherein selecting the one or more provided threshold indicators further includes determining whether the plurality of measurement values are statistically associated with the one or more conclusions.

10. The method of claim 6, wherein selecting the one or more provided threshold indicators includes determining for each threshold indicator one or more probabilities that the threshold indicator is indicative of the one or more conclusions.

11. The method of claim 1, further comprising providing the one or more threshold indicators.

12. The method of claim 1, wherein the plurality of conclusions comprise a focal conclusion and one or more alternative conclusions, and wherein each of the plurality of threshold indicators includes a first range of values indicative of the focal conclusion and a second range of values indicative of the one or more alternative conclusions.

13. The method of claim 12, wherein the pair of mutually exclusive and collectively exhaustive discriminators for each threshold indicator includes a first discriminator indicative of the focal conclusion and a second discriminator indicative of the one or more alternative conclusions.

14. The method of claim 12, wherein at least one of selecting the plurality of discriminators and ranking the plurality of discriminators is based on each discriminator's propensity to distinguish between the focal conclusion and the one or more alternative conclusions.

15. The method of claim 1, further comprising selecting one or more provided non-threshold indicators.

16. The method of claim 15, wherein selecting one or more provided non-threshold indicators includes determining for each non-threshold indicator one or more probabilities that the non-threshold indicator is indicative of the one or more conclusions.

17. The method of claim 15, wherein the plurality of discriminators includes multiple pairs of mutually exclusive and collectively exhaustive discriminators for each of the one or more provided non-threshold indicators.

18. The method of claim 15, wherein at least one of the provided non-threshold indicators comprises a result of a data analysis procedure performed on the training data set.

19. The method of claim 15, further comprising providing the one or more non-threshold indicators.

20. The method of claim 1, further comprising applying the sequence of discriminators to the one or more test data sets to select a conclusion from the plurality of conclusions for the one or more test data sets.

21. The method of claim 20, wherein the training data set comprises a plurality of data sources.

22. A method for selecting a conclusion from a plurality of conclusions using a sequence of provided discriminators, wherein the sequence of provided discriminators are selected and ranked from a plurality of discriminators into an ordered sequence, wherein at least one of selecting and ranking the portion of the plurality of discriminators includes: recalculating thresholds for one or more indicators; and generating new discriminators based on the recalculated thresholds, and wherein the plurality of discriminators includes a pair of mutually exclusive and collectively exhaustive discriminators generated for each of one or more threshold indicators associated with the conclusion, the method comprising:
applying the ordered sequence of provided discriminators to one or more test data sets to select the conclusion from the plurality of conclusions for the one or more test data sets.

23. A computer-readable medium having computer-executable instructions for performing a method for selecting a conclusion from a plurality of conclusions, the method comprising:
generating a plurality of discriminators from one or more provided threshold indicators associated with the conclusion, wherein the plurality of discriminators includes a pair of mutually exclusive and collectively exhaustive discriminators for each of the one or more provided threshold indicators;
selecting a portion of the plurality of discriminators; and
ranking the portion of the plurality of discriminators to create an ordered sequence of discriminators, wherein the ordered sequence of discriminators is for selecting the conclusion for one or more test data sets;
wherein at least one of selecting and ranking the portion of the plurality of discriminators includes:
recalculating thresholds for one or more indicators; and
generating new discriminators based on the recalculated thresholds.

24. A system for selecting a conclusion from a plurality of conclusions,
the system comprising:
a processor;
a memory coupled to the processor and storing instructions that, when executed by the processor, cause the processor to:
generate a plurality of discriminators from one or more provided threshold indicators associated with the conclusion, wherein the plurality of discriminators includes a pair of mutually exclusive and collectively exhaustive discriminators for each of the one or more provided threshold indicators;
select a portion of the plurality of discriminators; and
rank the portion of the plurality of discriminators to create an ordered sequence of discriminators, wherein the ordered sequence of discriminators is for selecting the conclusion for one or more test data sets;
wherein at least one of selecting and ranking the portion of the plurality of discriminators includes:
recalculating thresholds for one or more indicators; and
generating new discriminators based on the recalculated thresholds.

* * * * *